(12) United States Patent
Ye

(10) Patent No.: US 10,597,755 B2
(45) Date of Patent: *Mar. 24, 2020

(54) POROUS MATERIAL

(71) Applicant: CHONGQING RUNZE PHARMACEUTICAL CO., LTD., Chongqing (CN)

(72) Inventor: Lei Ye, Chongqing (CN)

(73) Assignee: CHONGQING RUNZE PHARMACEUTICAL CO., LTD., Chongqing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/752,584

(22) PCT Filed: Aug. 15, 2016

(86) PCT No.: PCT/CN2016/095328
§ 371 (c)(1),
(2) Date: Feb. 14, 2018

(87) PCT Pub. No.: WO2017/028771
PCT Pub. Date: Feb. 23, 2017

(65) Prior Publication Data
US 2018/0305791 A1 Oct. 25, 2018

(30) Foreign Application Priority Data
Aug. 18, 2015 (CN) .......................... 2015 1 0507154

(51) Int. Cl.
B32B 5/18 (2006.01)
C22C 1/08 (2006.01)
(Continued)

(52) U.S. Cl.
CPC ................ C22C 1/08 (2013.01); A61L 27/10 (2013.01); A61L 27/18 (2013.01); B01D 39/16 (2013.01);
(Continued)

(58) Field of Classification Search
None
See application file for complete search history.

(56) References Cited

U.S. PATENT DOCUMENTS

2001/0051833 A1* 12/2001 Walter ...................... A61F 2/28
623/23.58
2006/0002810 A1 1/2006 Grohowski, Jr.
(Continued)

FOREIGN PATENT DOCUMENTS

CN 101363085 A 2/2009
CN 101716368 A 6/2010
(Continued)

OTHER PUBLICATIONS

Ashby et al., "Metal Foams: A design guide", 2000, Butterworth-Heinemann, Section 4.4, p. 52-54 (Year: 2000).*
(Continued)

Primary Examiner — Seth Dumbris
Assistant Examiner — Kim S. Horger
(74) Attorney, Agent, or Firm — Knobbe, Martens, Olson & Bear LLP

(57) ABSTRACT

The present invention relates to a porous material, wherein the pores of the porous material are uniformly distributed. The uniform distribution of the pores means that the pores are evenly distributed at any unit-level volume of the porous material. The elastic modulus of the porous material is reduced by 10-99% compared to that of the raw material used to make the porous material. This kind of porous material ensures the uniformity of its various properties. It
(Continued)

Partial Enlarged View of A is a porous material with excellent performance and quality. Its uniformity also ensures that its elastic modulus can be effectively reduced to meet multiple purposes.

12 Claims, 2 Drawing Sheets

(51) Int. Cl.
| | |
|---|---|
| A61L 27/18 | (2006.01) |
| B01D 46/24 | (2006.01) |
| B33Y 80/00 | (2015.01) |
| A61L 27/10 | (2006.01) |
| B01D 39/16 | (2006.01) |
| B01D 39/20 | (2006.01) |
| H01M 4/66 | (2006.01) |
| H01M 4/80 | (2006.01) |
| H01M 4/86 | (2006.01) |
| B33Y 10/00 | (2015.01) |
| B23K 26/342 | (2014.01) |
| B23K 103/04 | (2006.01) |
| B22F 3/11 | (2006.01) |
| B29C 67/20 | (2006.01) |
| B29K 67/00 | (2006.01) |
| B29K 105/04 | (2006.01) |
| C25D 1/08 | (2006.01) |

(52) U.S. Cl.
CPC ..... *B01D 39/2027* (2013.01); *B01D 46/2429* (2013.01); *B33Y 80/00* (2014.12); *H01M 4/661* (2013.01); *H01M 4/808* (2013.01); *H01M 4/8605* (2013.01); *B01D 2046/2433* (2013.01); *B01D 2046/2437* (2013.01); *B01D 2239/10* (2013.01); *B01D 2239/1208* (2013.01); *B01D 2239/1291* (2013.01); *B22F 3/1137* (2013.01); *B22F 2301/10* (2013.01); *B22F 2301/20* (2013.01); *B23K 26/342* (2015.10); *B23K 2103/05* (2018.08); *B29C 67/202* (2013.01); *B29K 2067/046* (2013.01); *B29K 2105/04* (2013.01); *B33Y 10/00* (2014.12); *C25D 1/08* (2013.01)

(56) References Cited

U.S. PATENT DOCUMENTS

| | | | |
|---|---|---|---|
| 2010/0010513 A1* | 1/2010 | Yun | A61F 2/28 606/151 |
| 2014/0106181 A1* | 4/2014 | Nabawy | C22C 21/00 428/613 |
| 2014/0348688 A1* | 11/2014 | Bal | B22F 3/1134 419/2 |
| 2018/0236137 A1* | 8/2018 | Ye | C22C 1/08 |
| 2018/0236138 A1* | 8/2018 | Ye | A61L 27/02 |
| 2018/0237888 A1* | 8/2018 | Ye | C22C 27/04 |

FOREIGN PATENT DOCUMENTS

| | | | |
|---|---|---|---|
| CN | 102094224 A | | 6/2011 |
| CN | 102258805 A | | 11/2011 |
| CN | 102451911 A | | 5/2012 |
| CN | 102475902 A | | 5/2012 |
| CN | 102475903 A | | 5/2012 |
| CN | 102475904 A | | 5/2012 |
| CN | 102796892 B | | 12/2013 |
| CN | 104107097 A | * | 10/2014 |
| CN | 104357700 A | * | 2/2015 |
| EP | 2149414 A1 | | 2/2010 |

OTHER PUBLICATIONS

Zhang et al., "Elastic Modulus of Phases in Ti—Mo Alloys", 2015, Materials Characterization, 106, p. 302-307 (Year: 2015).*

* cited by examiner

Partial Enlarged View of A

B-B

POROUS MATERIAL

CROSS REFERENCE TO RELATED APPLICATIONS

This application is the national phase entry of International Application No. PCT/CN2016/095328, filed on Aug. 15, 2016, which is based upon and claims priority to Chinese Patent Application No. CN201510507154.4, filed on Aug. 18, 2015, the entire contents of which are incorporated herein by reference.

TECHNICAL FIELD

The present invention relates to a porous material.

BACKGROUND

The porous material is a new type of engineering material with excellent properties, combining both functional and structural properties, which is widely used in fields of metallurgical machinery, petrochemical industry, energy and environmental protection, national defense and military industry, nuclear technology and biopharmaceuticals, medical equipment, etc. For example, the porous material can be used for energy absorption, shock damping and noise reduction, such as in automotive bumpers and voice filters; the porous material can be used for filtration and separation of gas or liquid, so as to achieve the purification and separation of medium; the porous material can be used in heat exchangers having high efficiency; the porous material such as nickel foam, copper foam can be used as excellent electrode material for a variety of batteries, fuel cells and solar cells; the porous material such as porous titanium, porous tantalum, porous hydroxyapatite can be used as biomaterials, such as artificial bones, tooth, etc; the porous ceramics can be used as a catalyst carrier to promote the reaction; rigid polyurethane foam plastic can be used as thermal insulation materials, widely used in building energy saving; polymeric foam is used as a radome and a housing of radio transmitter.

At present, the application demands for many porous materials to have a uniform structure. That is, the pore size and the distribution of the pores are uniform, so that the performance is uniform. However, in fact, many porous materials fail to meet the requirements due to the lack of uniformity. Although some materials assert achieving higher uniformity through improvement, but the uniformity is only at a large volume scale, if compared under a small volume scale, for example, a plurality of three-dimensional blocks with volumes less than or equal to one cubic centimeter are randomly selected to measure the mass, the degree of uniformity is still very large. That is, the current porous material are only uniform at a large volume scale, but not uniform at a small volume scale. It can also be said that the nonuniformity at a small volume scale of the porous material causes the nonuniformity of various properties of the porous material such as strength, elastic modulus. Therefore the true elastic modulus of porous materials cannot be effectively reduced, thus seriously affecting its function.

SUMMARY OF THE INVENTION

The object of the present invention is to provide a highly uniform porous material whose elastic modulus can be effectively reduced.

The objective of the present invention is achieved by the following technical solutions.

A porous material with a uniform distribution of pores, characterized in that: the uniform distribution of pores means that the pores are evenly distributed at any unit-level volume of the porous material; and the elastic modulus of the porous material is reduced by 10-99% compared to that of the raw material used in the preparation of the porous material.

The unit-level volume refers to cubic centimeter level or cubic millimeter level or a lower unit-level volume.

The uniform distribution of pores means, when the three-dimensional blocks of the same size, not larger than 1 $cm^3$, are randomly taken from the porous material, then their masses are substantially equivalent.

The masses are substantially equivalent means that a plurality of three-dimensional blocks are randomly taken from a porous material having the same size of not more than 1 $cm^3$, to be respectively weighed and obtain an average of their masses. The absolute value of the mass deviation of any of the three-dimensional block from the average mass is not greater than 4% of the average mass of the three-dimensional blocks.

Preferably, a plurality of three-dimensional blocks of the same size not greater than 1 $cm^3$ in volume are randomly selected from the porous material, and weighed respectively to obtain an average value of their masses. The absolute value of the mass deviation of any three-dimensional block from the average value of the masses is not greater than 2% of the average mass of the three-dimensional blocks. Higher the uniformity, more stable will be the performance of porous material.

Preferably, if randomly take three-dimensional blocks of the same size not more than 1 $mm^3$ in volume from the porous material, and their masses are substantially the same. Similarly, substantially the same mass means a plurality of three-dimensional blocks of the same size not greater than 1 $mm^3$ in size taken from a porous material, and weighed respectively to obtain an average value of their masses. The absolute value of the mass deviation of any three-dimensional block from the average mass is not greater than 4% of the average mass of the three-dimensional blocks. Or, a more uniform case refers to a plurality of three-dimensional blocks of the same size not larger than 1 $mm^3$ taken from a porous material, and weighed respectively to obtain an average value of their masses. The absolute value of the mass deviation of any three-dimensional block from the average value of the masses is not greater than 2% of the average mass of the three-dimensional blocks.

The present invention further provides a porous material, which is composed of the pores classified into different levels according to the pore size of the material and cavity walls surrounding to form the pore. The cavity walls forming the upper-level large pores by surrounding three-dimensional space, are provided with lower-level small pores. The highly uniform porous material has more functions than a porous material with single pores, and the elastic modulus of the porous material can be controlled at different scales.

Preferably, the elastic modulus of the porous material is reduced by 50-99%.

Preferably, the elastic modulus of the porous material is reduced by 70-99%.

The advantages of the present invention are as below.

1. The uniformity of pore distribution of the porous material of the present invention is more specific than that mentioned in the prior art. The uniformity of the pore distribution of the porous material is required at a smaller unit-level volume scale, and the pores of such a porous material are highly uniform. Thus, ensuring the uniform consistency in the various properties of the porous material.

2. The porous material according to the present invention has a uniform pore distribution at a unit-level volume of cubic centimeter or cubic millimeter or a smaller unit. The masses are substantially equivalent so as to truly reduce the overall elastic modulus of the porous material.

BRIEF DESCRIPTION OF THE DRAWING

The present invention is further described below with reference to the accompanying drawings and embodiments.

DETAILED DESCRIPTION OF THE INVENTION

Figure 1:
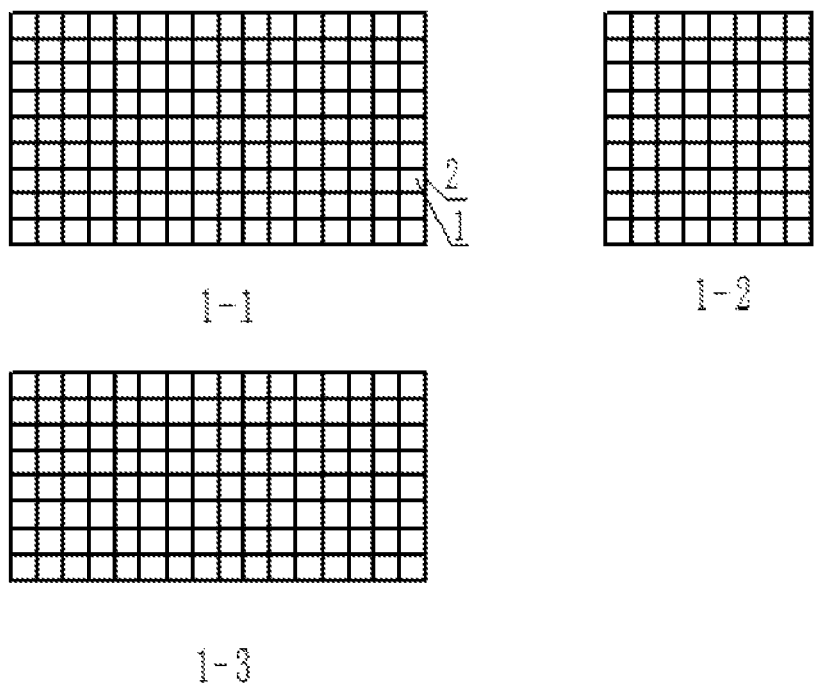
FIG. 1 is a structural schematic view of the porous material of the present invention, 1-1 is a front view, 1-2 is a left view, 1-3 is a top view.

The detailed embodiments are given on the premise of the technical solutions of the present invention, but the protection scope of the present invention is not limited to the following embodiments. Without departing from and changing the above technical idea of the present invention, according to common technical knowledge and/or usual means in the art, apparently various forms of substitutions and alterations can be made and should be included in the scope of the present invention As shown in FIG. 1, 1 is the pore, 2 is the cavity wall of the pore, the pores are uniformly distributed.

Figure 2:
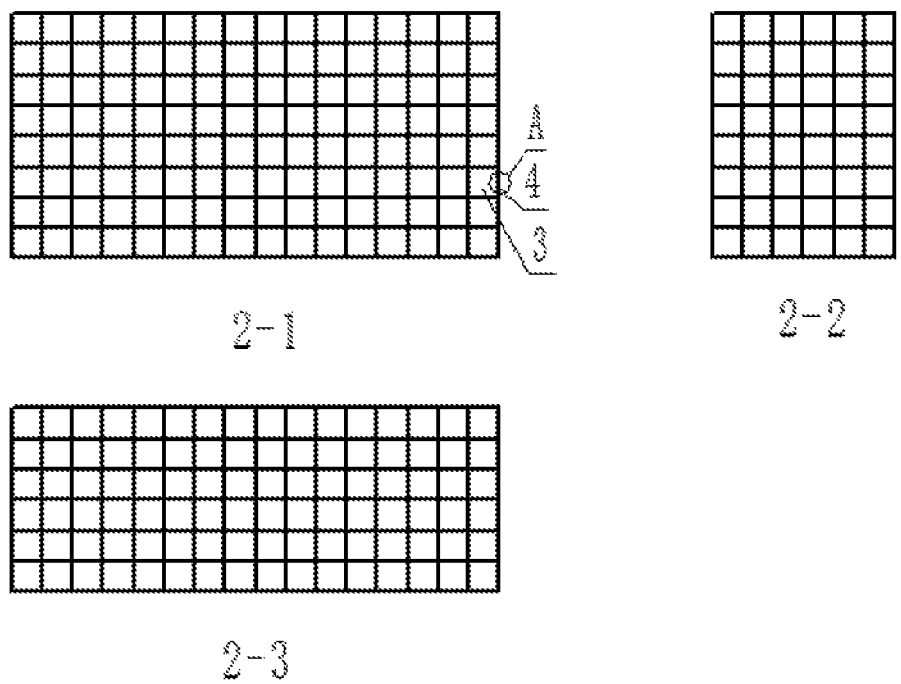
FIG. 2 is a structural schematic view of the porous material provided by embodiment 4 of the present invention, 2-1 is a front view, 2-2 is a left side view, 2-3 is a top view.
Figure 3:
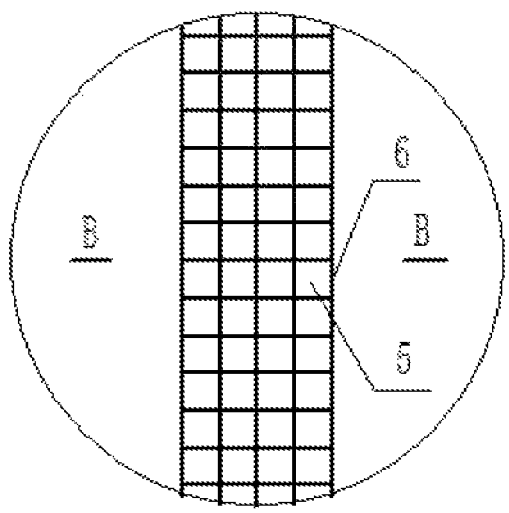
FIG. 3 is a partial enlarged view of A in FIG. 2.
Figure 4:
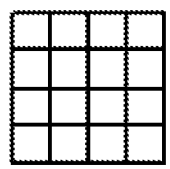
FIG. 4 is a B-B sectional view in FIG. 3.

As can be seen from FIG. 2 and FIG. 3, the cavity wall 4 of the pore 3 is formed by the smaller pores 5 (the next level pores) and the cavity wall 6 that is surrounding the pore 5. Referring to the enlarged view of the cavity wall 4 in FIG. 3 and the B-B sectional view in FIG. 4, the pore 5 is three-dimensionally interconnected, and the pores of two levels are also three-dimensionally interconnected.

The embodiment of the present invention are given below in detail.

Embodiment 1

The porous material of the present embodiment is porous stainless steel 316, the porosity of which is 75.5%, and composed of a square frame having a strut edge of 100 μm, a strut diameter of 30 μm and a unit of 12 strut edges. A cutting process is performed on the porous material to randomly get 10 pieces of three-dimensional blocks with the same size of 10 mm×10 mm×10 mm. Test their masses by a METTLER-TOLEDO XP26 Microbalance at an ambient temperature of 20° C. The measuring procedure is as follows.

1) Preheating: turn on the power, preheat the microbalance for a specified time.

2) The selection of basic mode of balance: tap the ON button, turn on the display, choose the "normal" mode.

3) Calibration: use Target (TAR) key to clear, use Calibration (CAL) minus and calibration weight to calibrate.

4) Weighing: press TAR key, the display is zero, then place the three-dimensional blocks successively on the scale pan, until the figure is stable, that is, the zero of the lower left corner of the display disappears, read the mass value of the three-dimensional block.

The measurement results are shown in Table 1, wherein the absolute value of the deviation from the average value is expressed as a percentage, the value is the absolute value of the deviation from the average divided by the average of masses. As shown in Table 1, the mass deviation is less than 4%.

TABLE 1

| Piece Number | Mass (mg) | Absolute Value of Deviation From the Average Value (%) |
|---|---|---|
| 1 | 1864.521 | 3.3% |
| 2 | 1912.954 | 1.7% |
| 3 | 1895.510 | 2.2% |
| 4 | 1909.078 | 1.5% |
| 5 | 1880.005 | 3% |
| 6 | 2013.737 | 3.9% |
| 7 | 1990.480 | 2.7% |
| 8 | 1973.037 | 1.8% |
| 9 | 1976.913 | 2% |
| 10 | 1963.346 | 1.3% |
| Average Mass | 1938.150 | |

According to GBT/7314-2005 "Metallic materials-Compression testing at ambient temperature", use the Instron mechanical testing machine to test the compressive stress-strain curve of the above porous stainless steel 316 with a compression test at ambient temperature of 25° C. The initial deformation shown by the stress-strain curve is an elastic deformation. The ratio of the stress value of the elastic deformation part to the corresponding strain value is taken as the elastic modulus, the value of the elastic modulus is 35.1 GPa, compared to the raw material used in the porous material, the elastic modulus is reduced by 82%.

A method of preparing the porous stainless steel 316 includes the following steps:

step 1: using powder of stainless steel 316 having substantially spherical particles with an average particle size of 10±2 μm;

step 2: using CAD software to make a square frame-shaped porous material model with strut edge of 102 μm, strut diameter of 30 μm and unit of 12 strut edges;

step 3: inputting the porous material model into the HRPM-IIB selective laser melting prototyping system, scanning according to the CAD software model with the scanning speed of 200 mm/min, when the laser beam completes a slice of area scanning, the cylinder is correspondingly descended by a thickness of the slice relative to the laser beam focal plane (forming plane), the thickness of slice is 30 μm;

step 4: proceeding stress relieving annealing; and step 5: proceeding abrasive blasting.

The kind of material is used to make the filter element.

Embodiment 2

The porous material of the present embodiment is porous nickel, having a porosity of 83% and an average pore diameter of 113 μm. A cutting process is performed on the porous material to randomly get 10 pieces of three-dimensional blocks with the same size of 10 mm×10 mm×8 mm. Testing their masses with a METTLER-TOLEDO XP26 Microbalance. The temperature and procedure of the testing are the same as that in embodiment 1. The results are shown in Table 2, wherein, the absolute value of the deviation from the average value is expressed as a percentage, the value thereof is the absolute value of the deviation from the average divided by the average of masses. As can be seen from Table 2, the mass deviation is less than 2%.

TABLE 2

| Piece Number | Mass (mg) | Absolute Value of Deviation From the Average Value (%) |
|---|---|---|
| 1 | 1225.532 | 0.39% |
| 2 | 1229.165 | 0.69% |
| 3 | 1200.100 | 1.69% |
| 4 | 1240.796 | 1.64% |
| 5 | 1224.320 | 0.29% |
| 6 | 1197.412 | 1.91% |
| 7 | 1219.475 | 0.1% |
| 8 | 1235.220 | 1.19% |
| 9 | 1226.740 | 0.49% |
| 10 | 1208.562 | 1% |
| Average Mass | 1220.632 | |

The elastic modulus of this kind of material measured by the method of Embodiment 1 is 15.6 GPa, which is 91% lower than that of the raw material used for the porous material.

The preparation method of porous nickel is as follows:

(1) substrate materials pretreatment: select a polyurethane foam with pore diameter of 152±3 μm, use hydrochloric acid for pretreatment;

(2) conductive treatment: use physical vapor deposition to deposit a layer of nickel on the polyurethane foam.

(3) electroplating: electroplate the polyurethane foam after conductive treatment with pulse current method, and electroplate the foam strut with nickel coating;

(4) reductive sintering: perform the reduction treatment in a protective atmosphere containing 70% of hydrogen and 30% of nitrogen to prepare a porous nickel material.

This kind of material is used to make electrodes.

Embodiment 3

The porous material of the present embodiment is a porous polylactic acid having a porosity of 66% and an average pore diameter of 20 μm. A cutting process is performed on the porous material to randomly get 10 pieces three-dimensional blocks with the same size of 1 mm×1 mm×1 mm. Measure the mass by a METTLER-TOLEDO XP26 Microbalance. The temperature and the procedure of measurement are the same as those in Embodiment 1, and the results are shown in Table 3. Wherein the absolute value of the deviation from the average value is expressed as a percentage, the value is the absolute value of the deviation from the average divided by the average mass. As shown in Table 3, the mass deviation is less than 4%.

TABLE 3

| Piece Number | Mass (mg) | Absolute Value of Deviation From the Average Value (%) |
|---|---|---|
| 1 | 0.440 | 0.5% |
| 2 | 0.437 | 1% |
| 3 | 0.425 | 3.8% |
| 4 | 0.438 | 0.8% |
| 5 | 0.437 | 1.2% |
| 6 | 0.449 | 1.5% |
| 7 | 0.459 | 3.9% |
| 8 | 0.451 | 2% |

TABLE 3-continued

| Piece Number | Mass (mg) | Absolute Value of Deviation From the Average Value (%) |
|---|---|---|
| 9 | 0.452 | 2.2% |
| 10 | 0.432 | 2.3% |
| Average Mass | 0.442 | |

With reference to GBT/1041-2008 "Plastics-Determination of compressive properties", the elastic modulus of this kind of material measured by the method of Embodiment 1 is 0.96 GPa, which is 68% lower than the elastic modulus of the raw material itself used in the porous material.

The preparation method of the porous polylactic acid is as follows:

(1) freezing the polylactic acid in liquid nitrogen and pulverizing the polylactic acid by a high-speed pulverizer, after that, to sieve particles with the particle size of 20 μm;

(2) selecting NaCl particles with a particle size of 20 μm;

(3) mixing the polylactic acid particles and NaCl particles in a weight ratio of 17:33, stirring the mixture at a speed of 60 r/min for 2 hours at 22° C. by a low-speed stirrer to mix them uniformly;

(4) putting the above mixture into a closed mould, pressing into blocks at 75° C. and at 7 MPa;

(5) immerse the above blocks in double distilled water for 72 hours, change the water every 6 hours, completely remove NaCl to obtain the porous polylactic acid.

This material is used to make medical implants.

Embodiment 4

The porous material of the present embodiment is the porous niobium with a secondary pore structure, which is classified into different levels according to the pore size of the material. All the pores are three-dimensionally interconnected, and the total effective porosity is 94%. The average pore size of large pores is 122 μm, and penetrating small pores with an average pore diameter of 10 μm were formed in the cavity walls of the large pores.

A cutting process is performed on the porous material to randomly get 9 pieces of three-dimensional blocks with the same size of 10 mm×10 mm×10 mm. Test the mass by a METTLER-TOLEDO XP26 Microbalance. The testing temperature and procedure are the same as those in Embodiment 1. The results are shown in Table 4, wherein the absolute value of the deviation from the average value is expressed as a percentage, the value is the absolute value of the deviation from the average divided by the average of masses. As shown in Table 4, the mass deviation is less than or equal to 4%.

TABLE 4

| Piece Number | Mass (mg) | Absolute Value of Deviation From the Average Value (%) |
|---|---|---|
| 1 | 512.845 | 1.3% |
| 2 | 513.365 | 1.2% |
| 3 | 504.011 | 3% |
| 4 | 508.169 | 2.2% |
| 5 | 510.247 | 1.8% |
| 6 | 498.816 | 4% |
| 7 | 532.590 | 2.5% |
| 8 | 529.992 | 2% |
| 9 | 524.796 | 1% |
| Average Mass | 519.600 | |

The elastic modulus of this kind of material measured by the method of Embodiment 1 is 1.05 GPa, which was 99% lower than that of the raw material used for the porous material.

The preparation method of porous niobium is as follows:

(1) material preparation using niobium powder with a particle size of 10 μm and urea with a particle size of 15 μm as pore-forming agent for the smallest pores, mixing uniformly and using starch with a particle size of 15 μm as a binder, a slurry is prepared by the niobium powder, urea, starch and distilled water mixed in the volume ratio of 1:1.5:1:7.

Filling the slurry uniformly into a polyester foam with a strut diameter of 160±3 μm by a foam impregnation method to form a green body; drying, and then pulverizing to obtain mixed grains with a particle size of 160±3 μm which contains niobium powder, a pore-forming agent and a polyester foam.

(2) Uniformly mixing the mixed grains and methylcellulose with a particle size of 160±3 μm in a volume ratio of 1:8, and filling the mixture into a closed mould to press into a compact green body.

(3) Sintering the compact green body at vacuum, and the sintered green body is subjected to conventional follow-up treatment according to the niobium process to obtain the porous niobium with secondary pores described in this embodiment.

This material is used to make medical implants.

Embodiment 5

The porous material of the present embodiment is porous copper with a porosity of 45.2% and an average pore diameter of 180 nm. A cutting process is performed on the porous material to randomly get 10 pieces of three-dimensional blocks with the same size of 1 mm×1 mm×1 mm. Test the mass by a METTLER-TOLEDO XP26 Microbalance. The temperature and the procedure of the measurement are the same as those in Embodiment 1. The results are shown in Table 5, wherein the absolute value of the deviation from the average value is expressed as a percentage, the value is the absolute value of the deviation from the average divided by the average of masses. As can be seen from Table 5, the deviation of mass is less than 2%.

TABLE 5

| Piece Number | Mass (mg) | Absolute Value of Deviation From the Average Value (%) |
|---|---|---|
| 1 | 4.730 | 0.8% |
| 2 | 4.725 | 0.9% |
| 3 | 4.706 | 1.3% |
| 4 | 4.692 | 1.6% |
| 5 | 4.715 | 1.1% |
| 6 | 4.859 | 1.9% |
| 7 | 4.820 | 1.1% |
| 8 | 4.811 | 0.9% |
| 9 | 4.825 | 1.2% |
| 10 | 4.801 | 0.7% |
| Average Mass | 4.768 | |

The elastic modulus of this kind of material measured by the method of Embodiment 1 was 99 GPa, which was 10% lower than that of the raw material used for the porous material.

The preparation method of porous copper is as follows:

(1) selecting polystyrene beads with a particle size of 200±4 nm;

(2) assembling the polystyrene beads into a three-dimensionally arranged colloid template;

(3) preparing the nanocrystalline copper solution;

(4) directly introducing the nanocrystalline copper solution into the three-dimensional colloid template made of polystyrene beads, and the solution infiltrates among the polystyrene beads;

(5) drying the mixture of three-dimensional colloid template/nanocrystalline copper solution;

(6) dissolving the polystyrene beads with chloroform to obtain the porous copper of this embodiment.

In the above preparation method, the nanocrystalline copper solution is prepared by using nanocrystalline copper powder with a particle size of 30-50 nm and deionized water, the concentration of the nanocrystalline copper solution is 0.08 g/ml, the drying temperature of mixture is 80° C.

This kind of material is used to make the target materials.

What is claimed is:

1. A porous material, comprising a plurality of pores in a uniform distribution, wherein each cubic centimeter of the porous material is uniform in mass, and an absolute value of a deviation of the each cubic centimeter of the porous material is equal to or less than 4% by mass, referring that when a plurality of three-dimensional blocks with a volume of equal to or less than 1 cm$^3$ and a same size are randomly taken from the porous material, each three-dimensional block of the plurality of three-dimensional blocks is weighed up respectively to obtain an average value of masses of the plurality of three-dimensional blocks, and the absolute value of the deviation of the each three-dimensional block from the average value of the masses is equal to or less than 4% of the average value of the masses of the plurality of three-dimensional blocks; and an elastic modulus of the porous material is reduced by 10-82% compared to a value of an elastic modulus of a raw material used to make the porous material.

2. The porous material according to claim 1, wherein the absolute value of the deviation of the each three-dimensional block from the average value of the masses is equal to or less than 2% of the average value of the masses of the plurality of three-dimensional blocks.

3. The porous material according to claim 1, wherein the porous material is composed of the pores classified into different levels according to a pore size and cavity walls surrounding to form the pores; the cavity wall forming upper-level large pores by surrounding a three-dimensional space are provided with lower-level small pores.

4. The porous material according to claim 1, wherein the elastic modulus of the porous material is reduced by 50 to 82%.

5. The porous material according to claim 3, wherein the elastic modulus of the porous material is reduced by 50 to 82%.

6. The porous material according to claim 1, wherein the elastic modulus of the porous material is reduced by 70 to 82%.

7. The porous material according to claim 3, wherein the elastic modulus of the porous material is reduced by 70 to 82%.

8. The porous material according to claim 2, wherein the elastic modulus of the porous material is reduced by 70 to 82%.

9. A porous material, comprising a plurality of pores in a uniform distribution, wherein each cubic millimeter of the porous material is uniform in mass, and an absolute value of a deviation of the each cubic millimeter of the porous material is equal to or less than 4% by mass, referring that when a plurality of three-dimensional blocks with a volume of equal to or less than 1 mm$^3$ and a same size are randomly taken from the porous material, each three-dimensional block of the plurality of three-dimensional blocks is weighed up respectively to obtain an average value of masses of the plurality of three-dimensional blocks, and the absolute value of deviation of the each three-dimensional block from the average value of the masses is equal to or less than 4% of the average value of the masses of the plurality of three-dimensional blocks; and an elastic modulus of the porous material is reduced by 10-82% compared to a value of an elastic modulus of a raw material used to make the porous material.

10. The porous material according to claim 9, wherein the absolute value of the deviation of the each three-dimensional block from the average value of the masses is equal to or less than 2% of the average value of the masses of the plurality of three-dimensional blocks.

11. The porous material according to claim 9, wherein the elastic modulus of the porous material is reduced by 70 to 82%.

12. The porous material according to claim 10, wherein the elastic modulus of the porous material is reduced by 70 to 82%.

\* \* \* \* \*